(12) United States Patent
Pitnick et al.

(10) Patent No.: US 8,303,300 B2
(45) Date of Patent: Nov. 6, 2012

(54) INTERMAXILLARY FIXATION BONDED BRACKET ASSEMBLY

(76) Inventors: Lewis Pitnick, Boca Raton, FL (US); Matthew J. Pitnick, Boca Raton, FL (US)

( * ) Notice: Subject to any disclaimer, the term of this patent is extended or adjusted under 35 U.S.C. 154(b) by 140 days.

(21) Appl. No.: 12/649,841

(22) Filed: Dec. 30, 2009

(65) Prior Publication Data

US 2010/0209866 A1    Aug. 19, 2010

Related U.S. Application Data

(60) Provisional application No. 61/153,161, filed on Feb. 17, 2009.

(51) Int. Cl.
*A61C 3/00* (2006.01)
(52) U.S. Cl. ................................................. 433/19
(58) Field of Classification Search ............ 433/8, 9, 433/10, 15, 19, 21, 2, 17, 18, 24, 148–149, 433/215; 292/259
See application file for complete search history.

(56) References Cited

U.S. PATENT DOCUMENTS

| | | | |
|---|---|---|---|
| 4,074,433 A | 2/1978 | Nelson | |
| 4,639,219 A | 1/1987 | Gagin | |
| 5,184,955 A | 2/1993 | Baer et al. | |
| 6,086,365 A | 7/2000 | Fields | |
| 6,669,474 B2 * | 12/2003 | Vogt | 433/19 |
| 7,927,097 B2 * | 4/2011 | Cervera Sabater et al. | 433/9 |
| 2003/0075186 A1 * | 4/2003 | Florman | 128/869 |
| 2009/0298003 A1 * | 12/2009 | Wei et al. | 433/9 |
| 2010/0092903 A1 * | 4/2010 | Sabilla | 433/2 |

* cited by examiner

*Primary Examiner* — Cris L Rodriguez
*Assistant Examiner* — Mirayada A Aponte
(74) *Attorney, Agent, or Firm* — Phillip Vales; Patent CEO

(57) ABSTRACT

An inter-maxillary fixation bracket having a top section having a mechanism for permitting attachment of a connection device and a base integrated with the top section where the base has grooves embedded on its underside for application of a dental adhesive such that a bracket can be fixed to a patient's tooth. An assembly includes a bracket with a connector attached to it utilizing a bracket connection mechanism, a linkage device, and another bracket and connector attached similarly. A method is also described for the immobilizing a patient's jaws including the modeling of a bracket assembly proximate to the patient's teeth to determine if the bracket assembly must be adjusted. And if so then adjustments to the linkage and connectors are made as appropriate. Adhesive is applied to bracket pads before attachment of the bracket pads to selected teeth and repeating the process for more brackets.

4 Claims, 5 Drawing Sheets

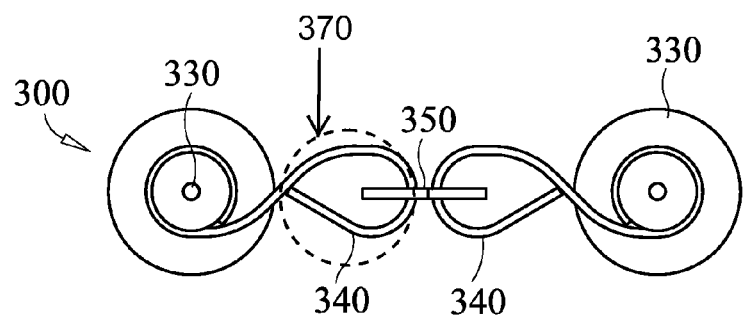
Fig. 3a
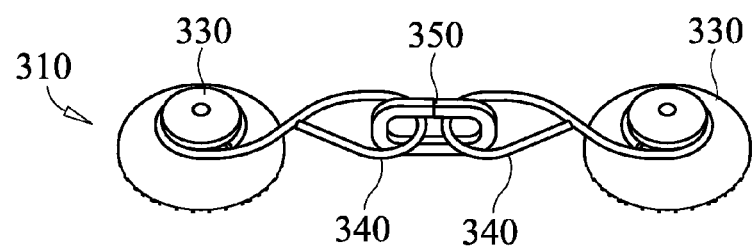
Fig. 3b
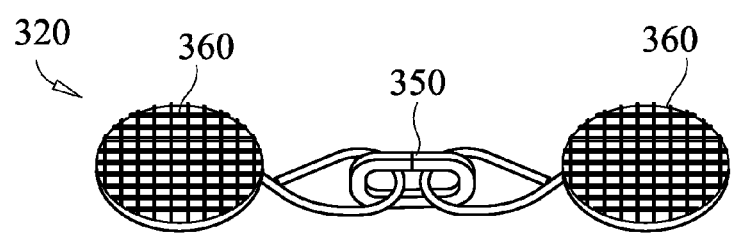
Fig. 3c
FIG. 3

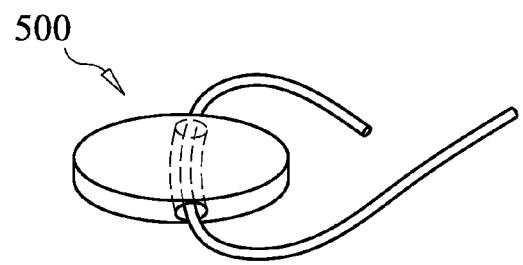
Fig. 5a
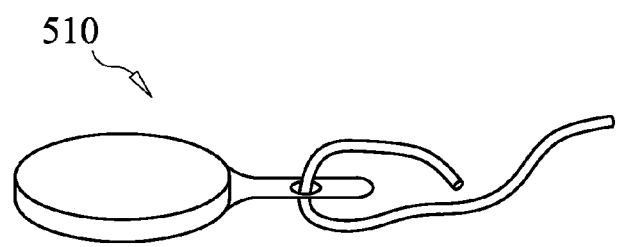
Fig. 5b
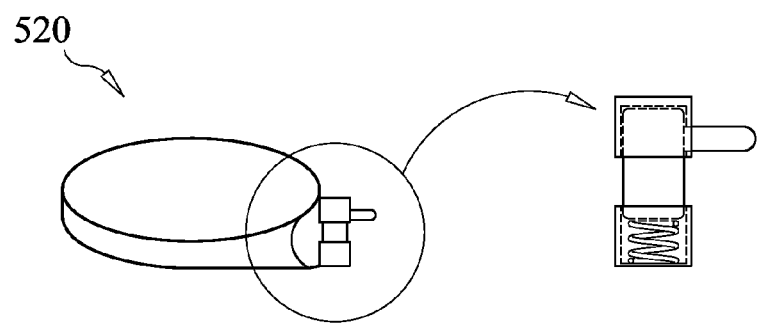
Fig. 5c
FIG. 5

INTERMAXILLARY FIXATION BONDED BRACKET ASSEMBLY

CROSS REFERENCE TO RELATED APPLICATIONS

This application is a child of U.S. provisional application 61/153,161 filed Feb. 17, 2009 and EFS ID 4807355 herein incorporated by reference.

STATEMENT OF FEDERALLY SPONSORED RESEARCH/DEVELOPMENT

Not Applicable

SEQUENCE LISTING, TABLE, OR COMPUTER PROGRAM APPENDIX ON COMPACT DISC & INCORPORATION BY REFERENCE

Not Applicable

BACKGROUND

1. Field of the Invention

Directed to dental improvements specifically relating to the immobilization of the jaw.

2. Description of the Related Art

U.S. Patent Citations

U.S. Pat. No. 4,074,433 discloses an orthodontic appliance for intermaxillary tooth correction comprising a pair of housings adapted to be connected to teeth in the upper and lower jaws respectively. Each housing has a pulley joined together by a pull cable with springs acting to draw the ends of the cable in opposite directions. The cables are wound in opposite directions so that the cable ends need not be centered in the housings. This facilitates assembly of the devices in which both are made of identical parts for ease of manufacture.

U.S. Pat. No. 4,639,219 discloses surgical ball hooks for intermaxillary fixation that are adjustably positionable on an archwire and which include a tubular base received by the archwire and an elongated bar or arm fixed at one end to the base and at right angles to the base and having its other end ball shaped. The tubular base may be seamless or split wherein the seamless version is mounted on the wire prior to placement of the wire and the split version may be mounted onto the wire subsequent to placement.

U.S. Pat. No. 5,184,955 discloses a device for the temporary fixation of teeth, teeth rows or jaw parts. The device has a wire (9), on which annular composite carriers (7) are movably arranged. The composite carriers (7) can, for example, be flexible synthetic material rings of cross-section in the form of a truncated cone, through which the wire (9) is guided by means of two holes (8) arranged in the walls, which lie opposite one another, of the composite carriers (7). The new splint makes possible the exact positioning of the composite carriers (7) which are arranged movably on the wire (9) and can be deformed at will by hand. After a caustic pretreatment of the tooth surface, the composite carriers (7), which are joined together by means of the wire (9), are placed on the teeth row to be connected and the cavities (A) of the composite carriers (7) are filled with composite (K) which surrounds on all sides the wire (9), which runs at a distance from the tooth surface, and connects both the wire (9) and the composite carriers (7) stably to the tooth surfaces. Use for the temporary fixation of traumatically dislocated teeth after their repositioning or for post-operative immobilization of jaw parts. The decisive advantage of the device is that it can be used not only by dentists, but also in particular by non-dentally trained personnel, that is to say emergency doctors, surgeons and auxiliary medical personnel.

U.S. Pat. No. 6,086,365 discloses fracture reduction and intermaxillary fixation being performed with a dental splint that is directly bonded by cement to the teeth of a patient for temporarily fixing and immobilizing the patient's jaws during and following oral surgery. The splint includes an arch band having a backside surface for receiving a deposit of bonding cement and a facial side surface from which multiple ligature studs project for engaging ligature wires. Each stud includes a tapered shank portion and a symmetrical head portion. The head portion of each stud is conformed for pivotal coupling engagement with a forceps tool. The arch band is intersected by multiple flow passages that permit bonding cement deposited on the back side surface of the arch band to flow or extrude onto the facial side surface as the arch band is pressed against the patient's teeth. Symmetrical construction of the head portions allows universal coupling engagement and manipulation by installation and de-bonding tools.

Current Techniques

The maxilla and mandible form the upper and lower jaw of a human being. The maxilla is a fusion of two bones that form the upper jaw holding the upper set of teeth in place whilst the mandible or inferior maxillary bone forms the lower jaw and holds the lower teeth in place. When a patient has fractured his or her jaw it becomes necessary to immobilize the mandible. In a procedure known as Intermaxillary Fixation, an Oral or Maxillofacial surgeon immobilizes the mandible to promote the healing process. Alternatively, this process can be used for radical weight reduction in cases of extreme need. In either case, current techniques suffer from various limitations including bleeding, discomfort, cost and the difficulty of removal of the dental devices. Currently, there are three main methods of accomplishing the Intermaxillary Fixation; these are namely, the use of bone-supported techniques (Cortical Bone Screws, hanger plates, inter-arch mini-plates), the Arch Bar method and the use of Ernst Ligatures.

FIG. 1 illustrates the prior art apparatus as applied to the jaw and teeth of a patient for immobilizing the jaw and teeth of a patient utilizing an arch bar apparatus 100 in one view and a cortical bone screw apparatus 110 in the other drawing. Item 100 shows the jaws and teeth of a patient that have been immobilized using an arch bar apparatus 120. The arch bar 120 is made up of two bars placed in contact with the upper and lower sets of teeth as generally shown in FIG. 1. For the sake of clarity, drawing 100 illustrates the arch bars before they have been placed over the teeth of the patient. A dental professional moves these over the teeth and interlaces them with wiring so as to fix the jaw in place.

Item 110 depicts the jaws and teeth of a patient that have been immobilized using the prior art apparatus know as a cortical bone screw 130. Another method of immobilizing the maxilla and mandible utilizes the cortical bone screw system. The cortical bone screw system 130 utilizes several bone screws to penetrate the lower and upper jaws of a patient. Once fixed to the patient's mandible and maxilla these screws are used to shut the patient's jaw through the use of wires that are tightened around the various screws passing up, down and around the screws at the discretion of the medical practitioner.

The final common technique for immobilizing the mandible uses what are known as Ernst Ligatures. In this method, a wire is passed through the inter-dental space of neighboring teeth in the same segment of one dental arch and further threaded a few times until a closed loop can be tightened. Ligatures are added as needed on the different sides of the mouth that leads to the final closure of the mouth by a dental professional twisting the ends of the wires together as needed.

All of the aforementioned techniques suffer from various disadvantages including but not limited to: painful application of the device, bleeding, possibility of infection, great discomfort and cost of the materials.

SUMMARY OF THE INVENTION

An inter-maxillary fixation bracket describing a top section having a mechanism for permitting attachment of a connection device and a base integrated with the top section where the base has a means embedded on its underside for application of a dental adhesive such that a bracket can be fixed to a patient's tooth. The mechanism for permitting attachment of a connection device is selected from a group of mechanisms such as a narrow neck integrated with the top section, a cavity in the top section for passage of a connection device, a jewelers spring loaded locking mechanism in the top section and a post with cavity for threading of a connection device. Further, a system is provided that has one or more connectors and optionally one or more linkage devices. However, there are preferably at least two brackets, two connectors and one linkage device.

A method is also described for the immobilizing the jaw of a patient including the modeling of the bracket assembly proximate to the patient's teeth to determine if the bracket assembly must be adjusted. And if the determining step determines that an adjustment must be made then adjustments to the linkage and connectors are made as appropriate. Next, adhesive is applied to two bracket pads before attachment of the bracket pads to selected teeth. Then if it is determined that there are more brackets needed then the process repeats again from the modeling step otherwise ending the method. In the event that no adjustments were necessary the adjustment step is bypassed.

BRIEF DESCRIPTION OF THE DRAWINGS

FIG. 3a illustrates the top view of the Inter-maxillary Bonded Bracket Assembly.

FIG. 3b illustrates the side view of the Inter-maxillary Bonded Bracket Assembly.

FIG. 3c illustrates the underside view of the Inter-maxillary Bonded Bracket Assembly.

FIG. 5a illustrates an alternative bracket embodiment.
FIG. 5b illustrates an alternative bracket embodiment.
FIG. 5c illustrates an alternative bracket embodiment.

DESCRIPTION OF THE PREFERRED EMBODIMENTS

Figure 1A:
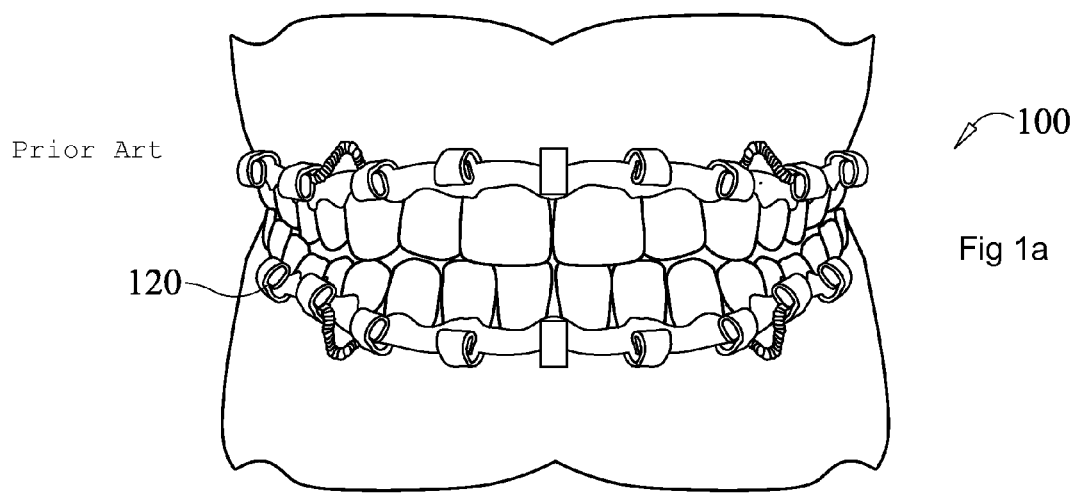
FIG. 1a illustrates the prior art apparatus for immobilizing the jaw and teeth of a patient utilizing an arch bar.
Figure 1B:
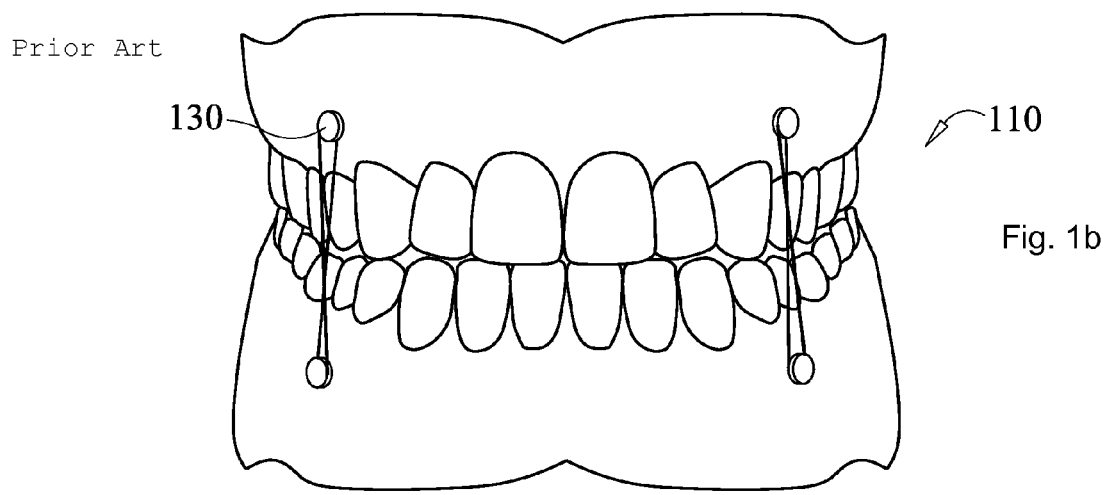
FIG. 1b illustrates the prior art apparatus for immobilizing the jaw and teeth of a patient utilizing a cortical bone screw
Figure 2A:
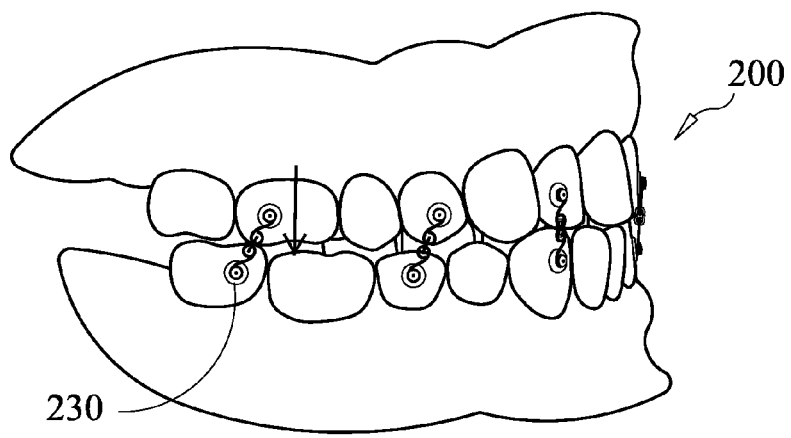
FIG. 2a illustrates the Inter-maxillary Bonded Bracket Assembly as applied to the side view of a patient's teeth.
Figure 2B:
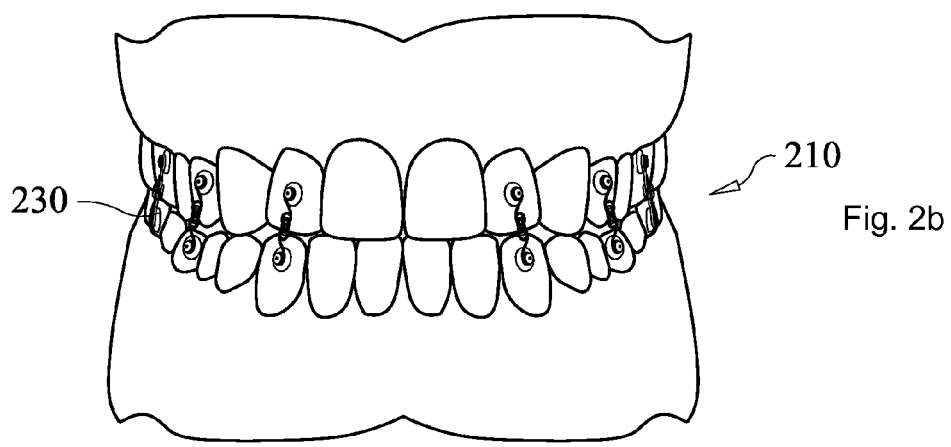
FIG. 2b illustrates the Inter-maxillary Bonded Bracket Assembly as applied to the front view of a patient's teeth.
Figure 2C:
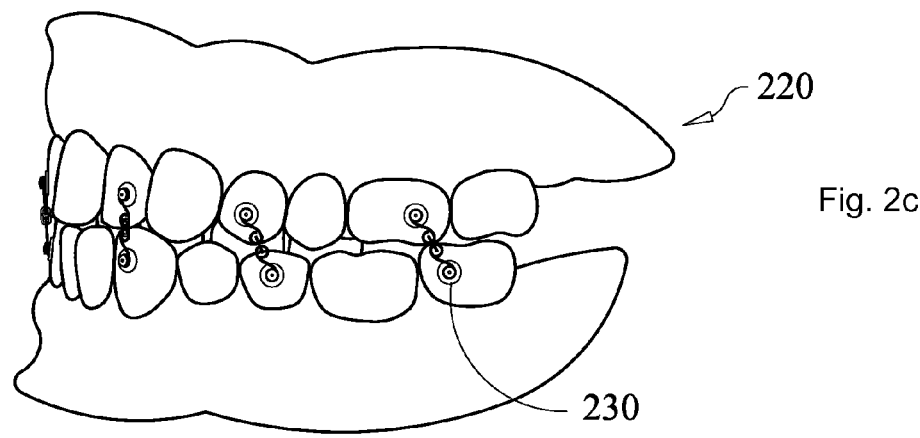
FIG. 2c illustrates the Inter-maxillary Bonded Bracket Assembly as applied to the side view of a patient's teeth.
Figure 4:
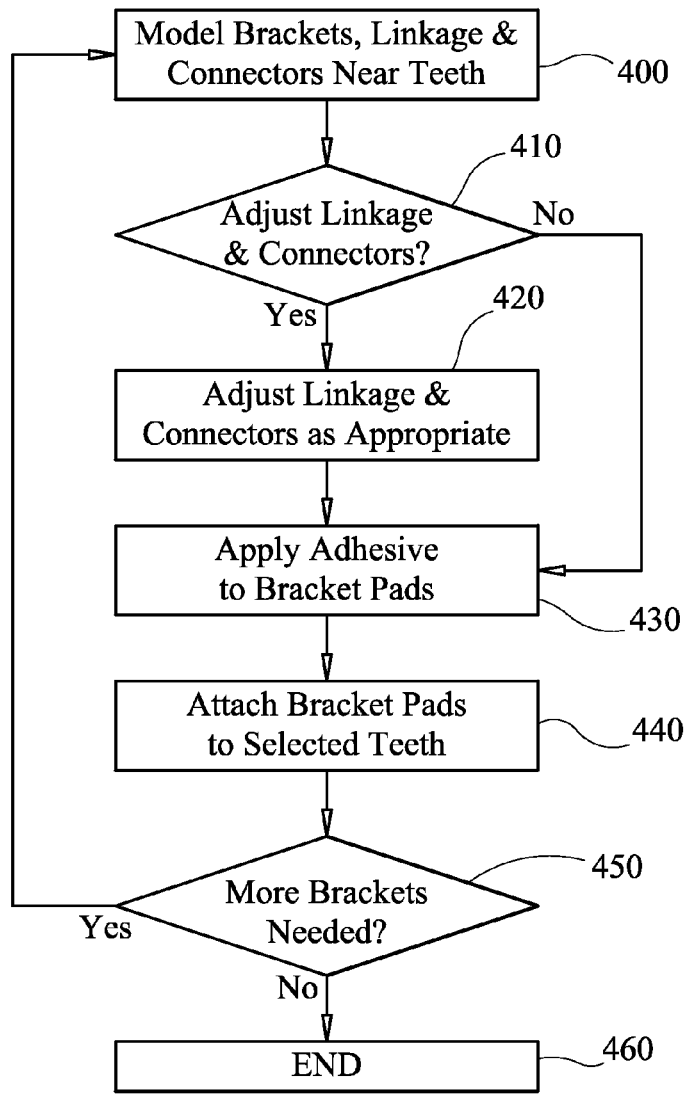
FIG. 4 illustrates a method for applying the Inter-Maxillary Bonded Bracket Assembly to a patient's teeth.

The following discussion of FIGS. 2-4 describes the preferred embodiment of the Inter-maxillary Bonded Bracket Assembly.

FIG. 2:

FIG. 2 illustrates the standalone Inter-maxillary Bonded Bracket Assembly as applied to the front and two side views of a patient's teeth. Each bracket is applied to a single tooth (in other words each bracket stands alone on the tooth) as shown so that a preferred assembly has two brackets (plus connectors and linkage) attached to two teeth through the use of dental adhesive on the underside of the bracket in contact with each tooth. A right side view of a patient's teeth 200 illustrates several Inter-maxillary Bonded Bracket Assemblies 230 arranged in angled patterns. The assemblies are preferably angled downwards and towards the back of the patient's mouth for immobilization of the mandible. Next, a frontal view of a patient's teeth 210 illustrates several Inter-maxillary Bonded Bracket Assemblies 230 arranged in angled patterns. Again, the assemblies are preferably angled downwards and towards the back of the patient's mouth for immobilization of the mandible. The assemblies 230 become more and more vertical as they approach the front of the mouth as shown in the diagram. In the last view, a left side view of a patient's teeth 220 illustrates several Inter-maxillary Bonded Bracket Assemblies 230 arranged in angled patterns. Finally, the assemblies are preferably angled downwards and towards the back of the patient's mouth for immobilization of the mandible.

FIG. 3: 300:

FIG. 3 illustrates the Inter-maxillary Bonded Bracket Assembly (300, 310, 320) in several views including top, side and underside views. The Inter-maxillary Bonded Bracket Assembly 300 is shown in a topside view. The assembly 300 preferably has first and second brackets 330, first and second 'S' connectors 340, and a linkage 350 in a unique arrangement for immobilizing the mandible. Starting from the left side of the assembly 300, it is important to point out that the attachment mechanism used by the assembly is a raised section of the first bracket 330 that extends out of the lower section of the same. At the top of first bracket 330 is a circular artifact of the manufacturing process that is shown only as a cosmetic illustration of the attachment mechanism. The raised section forms a 'top section' and is a stud for wrapping a wire about in a simple but effective fashion. The first 'S' connector 340 is a wire preferably of some reliable metallic material useful in dental procedures with all of the accompanying requirements of such a working environment. It is wrapped in a circular pattern about the stud ('top section') of the leftmost bracket 330 and more specifically around the neck of the raised stud section of the same. This end of the 'S' connector is wound loosely enough to permit easy movement about the stud neck in a circular motion about the vertical axis of the bracket 330. Additionally, the end of the 'S' connector 340 that wraps around the stud neck terminates in sufficient closure so as to avoid the device from disengaging from the stud neck.

The other side of the 'S' connector 340 is arranged in a teardrop shape 370 in association with a linkage 350 as shown in 300. This teardrop shape (and in the later discussion with regards to the other connector and also the other side of each connector) is shown optimally whilst the most generic rendering of this connection (and each of the ends of both connectors) has it as a loop (s) (ellipse, circle, general curve) or wire segment(s) (a straight wire segment integrally combined with another wire segment and or curve(s)). The wire connector teardrop section 370 is threaded through an oblong linkage 350 and is folded back towards the middle of the leftmost connector 340 with sufficient closure of the teardrop to avoid the linkage 350 from slipping out of the 'S' connector 340; this closure is at least smaller than the width of the diameter of the linkage 350 shown in the drawing or actually approaches or reaches zero closure. The oblong linkage may have other shapes depending on the material used such as rectangular, curved, round, oval, square, teardrop, trapezoidal, and an ellipse.

As it bends backwards, the end of the connector 340 preferably makes physical contact (total closure—may also be somewhat open depending upon the dental practitioner requirements) with the connector itself approximately at the middle of the 'S' connector. The linkage 350 previously described is the centerpiece of the Inter-maxillary Bonded Bracket Assembly 300. It is an oblong rectangular linkage that has rounded rectangular edges with two ends that bend back towards each so as to form the rectangular shape of the linkage 350; it should be noted that this makes this linkage easily removable in the event that a patient emergency arises since it is simply a matter of bending or cutting the linkage to separate the two connectors from each other. The ends reach closure and are preferably in physical contact with each other or at least with a separation smaller than the diameter of the wire 'S' connectors 330 so as to avoid the disengagement of one or more of the connectors 330 from the linkage 350.

On the right side of the linkage 350 is a second 'S' connector 340 forming another teardrop as shown in 300. The end of the teardrop is threaded through the right side of linkage 350 and bent back towards the middle of the second connector 340. It is folded back towards the middle of the rightmost connector 340 with sufficient closure of the teardrop to avoid the linkage 350 from slipping out of the 'S' connector 340; this closure is at least smaller than the width of the diameter of the linkage 350 shown in the drawing or actually approaches or reaches total closure. As it bends backwards, the end of the connector 340 preferably makes physical contact (total closure) with the connector itself approximately at the middle of the 'S' connector.

Ending on the right side of the assembly 300, it is important to point out that the final attachment mechanism used by the assembly is a raised section of the second bracket 330 that extends out of the lower section of the same. At the top of second bracket 330 is a circular artifact of the manufacturing process that is shown only as a cosmetic illustration of the attachment mechanism. The raised section is a stud for wrapping a wire about in a simple but effective fashion. The second 'S' connector 340 is a wire preferably of some reliable metallic material useful in dental procedures with all of the accompanying requirements of such a working environment. It is wrapped in a circular pattern about the stud of the rightmost bracket 330 and more specifically around the neck of the raised stud section of the same. This end of the rightmost 'S' connector is wound loosely enough to permit easy movement about the stud neck in a circular motion about the vertical axis of the right bracket 330. Additionally, the end of the rightmost 'S' connector 340 that wraps around the stud neck terminates in sufficient closure so as to avoid the device from disengaging from the stud neck.

It should be apparent that the simplicity of the entire Inter-maxillary Bonded Bracket Assembly permits wide latitude for its application in the many different sets of teeth that a dental practitioner finds in the real world. In particular, the ability to alter the movement of parts for the varying conditions found on each patient from total restriction of motion to a lesser restrictive application allows for situational awareness that perfectly describes the dental art. In the first case, that of total restriction of movement, a practitioner would ensure that the mandible is absolutely restricted from moving whatsoever. Here the assembly is wound as tightly as physically possible with no possibility of motion about the axis of the brackets 330, nor movement of the two connectors 340 in the linkage 350. In the second case, depending upon the needs of the patient, the dental practitioner tightens the different parts (330, 340 and 350) together with varying degrees of restriction or looseness. Then, using a dental adhesive applied to the bottoms of the brackets 330, the practitioner applies the Inter-maxillary Bonded Bracket Assembly to the teeth of a patient so as to effect the immobilization of the mandible. Then he or she applies one or more (preferably several) assemblies across the teeth of the patient in a manner that provides the best fit and stabilization for the particular circumstances encountered in the patient's unique dental requirements.

FIG. 3: 310:

The Inter-maxillary Bonded Bracket Assembly 300 is shown in a side view. The assembly 310 preferably has first and second brackets 330, first and second 'S' connectors 340, and a linkage 350 in a unique arrangement for immobilizing the mandible. Starting from the left side of the assembly 310, it is important to point out that the attachment mechanism used by the assembly is a raised section of the first bracket 330 that extends out of the lower section of the same. At the top of first bracket 330 is a circular artifact of the manufacturing process that is shown only as a cosmetic illustration of the attachment mechanism. The raised section is a stud for wrapping a wire about in a simple but effective fashion. The first 'S' connector 340 is a wire preferably of some reliable metallic material useful in dental procedures with all of the accompanying requirements of such a working environment. It is wrapped in a circular pattern about the stud of the leftmost bracket 330 and more specifically around the neck of the raised stud section of the same. This end of the 'S' connector is wound loosely enough to permit easy movement about the stud neck in a circular motion about the vertical axis of the bracket 330. Additionally, the end of the 'S' connector 340 that wraps around the stud neck terminates in sufficient closure so as to avoid the device from disengaging from the stud neck.

The other side of the 'S' connector 340 is arranged in a teardrop shape in association with a linkage 350 as shown in 310. The wire connector teardrop section 370 is threaded through an oblong linkage 350 and is folded back towards the middle of the leftmost connector 340 with sufficient closure of the teardrop to avoid the linkage 350 from slipping out of the 'S' connector 340; this closure is at least smaller than the width of the diameter of the linkage 350 shown in the drawing or actually approaches or reaches zero closure. As it bends backwards, the end of the connector 340 preferably makes physical contact (total closure) with the connector itself approximately at the middle of the 'S' connector. The linkage 350 previously described is the centerpiece of the Inter-maxillary Bonded Bracket Assembly 310. It is an oblong rectangular linkage that has rounded edges with two ends that bend back towards each so as to form the rectangular shape of the linkage 350; it should be noted that this makes this linkage easily removable in the event that a patient emergency arises since it is simply a matter of bending or cutting the linkage to separate the two connectors from each other. The ends reach closure and are preferably in physical contact with each other or at least with a separation smaller than the diameter of the wire 'S' connectors 330 so as to avoid the disengagement of one or more of the connectors 330 from the linkage 350.

On the right side of the linkage 350 is a second 'S' connector 340 forming another teardrop as shown in 310. The end of the teardrop is threaded through the right side of linkage 350 and bent back towards the middle of the second connector 340. It is folded back towards the middle of the rightmost connector 340 with sufficient closure of the teardrop to avoid the linkage 350 from slipping out of the 'S' connector 340; this closure is at least smaller than the width of the diameter of the linkage 350 shown in the drawing or actually approaches or reaches total closure. As it bends backwards, the end of the connector 340 preferably makes physical contact (total closure) with the connector itself approximately at the middle of the 'S' connector.

Ending on the right side of the assembly 310, it is important to point out that the final attachment mechanism used by the assembly is a raised section of the second bracket 330 that extends out of the lower section of the same. At the top of second bracket 330 is a circular artifact of the manufacturing process that is shown only as a cosmetic illustration of the attachment mechanism. The raised section is a stud for wrapping a wire about in a simple but effective fashion. The second 'S' connector 340 is a wire preferably of some reliable metallic material useful in dental procedures with all of the accompanying requirements of such a working environment. It is wrapped in a circular pattern about the stud of the rightmost bracket 330 and more specifically around the neck of the raised stud section of the same. This end of the rightmost 'S' connector is wound loosely enough to permit easy movement about the stud neck in a circular motion about the vertical axis of the right bracket 330. Additionally, the end of the rightmost 'S' connector 340 that wraps around the stud neck terminates in sufficient closure so as to avoid the device from disengaging from the stud neck. Finally, at the bottom of each of the brackets 330 are shown artifacts of a pattern of perpendicular ridges to be described in connection with FIG. 3: 320.

FIG. 3: 320:

The Inter-maxillary Bonded Bracket Assembly 320 is shown in a bottom view. The assembly 320 preferably has first and second brackets shown upside down 360 ('base section' or bottom section), first and second 'S' connectors, and a linkage 350 in a unique arrangement for immobilizing the mandible. With respect to the connectors and linkage no more discussion is necessary since these were discussed exhaustively with respect to FIG. 3 (300, 310). At the bottom of each of the brackets are shown a pattern of perpendicular ridges 360 ('base or bottom section') that aid in the adhesion of the dental adhesive. These ridges are simply a set of crossing perpendicular rows that form multiple depressions across the face of the bottom of the bracket as shown. When a dental practitioner applies dental adhesive to the bottom of the bracket across the perpendicular ridges the adhesive enters the depressions and forms a firmer bond with the bracket because of the increased surface area. The dental practitioner would then apply the set of brackets to a patient's teeth as shown in the various views of FIG. 2 or as required by the specific requirements (in number and physical arrangement) of each and every particular patient.

FIG. 4:

FIG. 4 illustrates a method for applying the Inter-Maxillary Bonded Bracket Assembly to a patient's teeth. The process begins with the modeling 400 of the brackets, linkage and connectors near or on the teeth of the patient. Before the bracket, connectors, and linkage are applied to a patient's teeth a dental professional poses them near the intended teeth so as to ascertain the proper fit of the assembly. Depending upon the results of this modeling, he or she adjusts the linkage and connectors 410 as needed. If no adjustments were necessary then the process skips to step 430. On the other hand, if there were any necessary adjustments to the linkage and connector the process proceeds to step 420 whereby a dental professional adjusts linkage and connectors as appropriate. In either case, the process moves on to step 430.

At this step, adhesive is applied 430 to the back of two bracket pads (more if necessary) so as to permit the attaching of the two bracket pads to selected teeth 440. If no more brackets assemblies are needed 450 to complete the immobilization then the process repeats by remodeling the bracket(s) (one or more), linkage and connectors near the teeth 400 as before. If no more brackets are needed to immobilize the jaw then the process ends 460. It should be noted that whilst a bracket assembly is typically composed of two brackets, two connectors and a linkage, this method permits for more than two brackets (as well as more than two connectors and more than one linkage) to be connected in the event such is desired for the unique circumstances encountered in the field. A dental professional would simply use more connectors, linkages, and brackets as needed.

Materials and Manufacturing: The following materials and manufacturing processes are for informational purposes only.

Adhesive: the dental adhesive used to bond the bracket assembly is a generic or typical dental adhesive such as a moisture activated adhesive, light cured adhesive or other such dental adhesive. There are many different types of adhesives and curing methods available in dentistry. The appropriate application is to follow the brand manufacturers instructions for use.

Assembly: The assemblies are supplied to doctors in a standard or special configuration. Whilst the standard configuration is sufficient for most patients, the doctor specifies the bracket style and composition, the type of connector and the method of linkage. Of course, the assembly as described in this patent is a manual process requiring specialized tools and equipment to join the components together.

Brackets: Brackets 330 are made of metal(s), alloy(s) or combination of the foregoing. Other implementations permit the use of ceramic(s) and or plastic(s) in the manufacture of the brackets.

Connectors: Connectors 340 are made of metal(s), alloy(s) or combination of the foregoing. Other materials combinations are envisioned including plastic, silicone, elastics and or plastics.

Linkage: linkage 350 is made of plastic, polymers, gold, silicone, metal(s), alloy(s) or combination of the foregoing.

Manufacturing Techniques:

Brackets: The brackets are manufactured using different methods including machining, casting and or molding as some examples.

Linkage: Plastic or elastic links can be extruded or molded. Metal or alloy linkage are manufactured using a sequential series of dies in that the next die has a smaller opening then the previous die. Wire is drawn through each die reducing its diameter until the required diameter is reached. Annealing or heating of the wire is required at various steps to reduce brittleness and to achieve a usable temper. The wire is then formed to the required shape and cut to size. The wire is then formed to the required shape, cut to size forming a link. The two ends are sealed together to form a closed shape. Another method for a metal or alloy is to roll the metal to a desired thickness and then stamp, cut or chemical etch the required shape in the flat stock.

Connectors: Plastic or elastic connectors can be extruded or molded. Metal or alloy connectors are manufactured using a sequential series of dies in that the next die has a smaller opening then the previous die. Wire is drawn through each die reducing its diameter until the required diameter is reached Annealing or heating of the wire is required at various steps to reduce brittleness and to achieve a usable temper. The wire is then formed to the required shape and cut to size.

OTHER CONSIDERATIONS AND ALTERNATIVE EMBODIMENTS

Alternative embodiments of the Inter-Maxillary Assembly use bracket devices that are replaced with alterative brackets as described in the following section. Also, other embodiments use sections of the device instead of the entire system. Finally, the shape of the different parts is alterable based upon manufacturing needs, patient desires, and or practitioner requirements.

Alternative Brackets:

The brackets utilize, in one alternative embodiment 500, a cavity instead of a neck wiring arrangement to attach the connectors to the bracket. In this particular alternative, a hole is punched through the stud or if no stud exists the body of the bracket itself; further, if no stud exists as in the latter case, the bracket is shaped to be as unobtrusive as possible for the patient (typically a bubble or dome like shape). One end of the connector is threaded through this hole or cavity and returns to the center of the connector body. Another embodiment uses a post with a hole 510 attached to the base so as to thread the connector there through as in the first alternative embodiment above. Finally, in another embodiment a tiny spring loaded lock 520 is useable to engage closure of the threaded connector wire at the bracket device as in an item of jewelry.

Shapes:

Different shapes are useable based upon the needs of the patient and flexibility of application. For example, the connectors attachment section whether to the linkage or to the brackets are capable of being shaped in the following forms: circular, curved, elliptical, shape sensitive, tear-dropped, or combinations of the foregoing. Shape sensitive means wires shaped according to the shape of the different parts as described below. The bracket can be shaped as needed by the practitioner or patient in many forms as follows: circular, curved, elliptical, regular or irregular polygonal, square, tear-dropped, individual tooth-shaped (following the lines of the different teeth), trapezoidal, triangular, or combinations of the foregoing. Additionally, if using the embodiment with the neck and stud (or base and post) the base of the bracket and stud (or base and post) can be made of different shapes as described in this paragraph above to suit the particular needs and or wants of the patient and or practitioner. Finally, the perpendicular patterns of grooves found at the bottom of the base of the various brackets described herein are replaceable with other arrangements of grooves or depressions. For example, diagonal lines grooves, pitted circular depressions, irregular or regular polygonal shaped depressions, curved, elliptical, or more generally a regular array of depressions.

CONCLUSION

There are many improvements and novelties that have been shown as a result of the novel teachings taught herein. Some of these include improvements in placement, bonding ability, size reduction, shapes, non-invasiveness, and the ease of removal. The ability to swivel provides for flexibility in the placement of the device on opposing teeth. The mesh pad affords great strength in bonding of the bracket to the tooth. Next, the small size and variety of shapes accommodates placement variability. Additionally, since the assembly is non-invasive there is a reduced exposure to complications. Finally, patient emergencies are easily handled since the linkage is easily cut or removed.

Thus, the Inter-maxillary Bonded Bracket Assembly overcomes the prior art deficiencies by providing for cost reduction since there are fewer materials involved, eliminating the bleeding and pain found in many prior art approaches since it non-invasive, and improving user friendliness since the linkage can be easily removed in the case of emergency.

We claim:

1. An inter-maxillary fixation bracket assembly comprising:
    a top section having a mechanism attached to an S Shaped connection device that swivels about the mechanism and
    a base integrated with the top section where the base has grooves embedded on its underside for application of a dental adhesive whereby the bracket can be fixed to a patient's tooth such that the mechanism attached to the S Shaped connection device is a narrow neck integrated with the top section.

2. The inter-maxillary fixation bracket assembly of claim 1 further comprising:
    a linkage device connected to the first S Shaped connection device on one side.

3. The inter-maxillary fixation bracket assembly of claim 2, further comprising:
    a second connection device connected to the linkage device on another side of the linkage means.

4. The inter-maxillary fixation bracket assembly of claim 3, further comprising:
    a second bracket assembly having a base section for dental adhesive application and further attached to the second connector means.

* * * * *